United States Patent [19]
Kitrilakis et al.

[11] 3,951,143
[45] Apr. 20, 1976

[54] INTERMITTENT DEMAND VENTILATOR

[75] Inventors: Sotiris Kitrilakis; Thomas C. Robinson, both of Berkeley, Calif.

[73] Assignee: Searle Cardio-Pulmonary Systems Inc., Emeryville, Calif.

[22] Filed: Nov. 20, 1974

[21] Appl. No.: 525,291

[52] U.S. Cl. ................. 128/145.8; 128/DIG. 17
[51] Int. Cl.² .......................... A61N 16/00
[58] Field of Search.......... 128/145.8, 145.6, 145.5, 128/142.2, 142.3, 142.4, 146.5, 202, 203, 188, DIG. 17

[56] References Cited
UNITED STATES PATENTS

| | | | |
|---|---|---|---|
| 3,138,152 | 6/1964 | Wilson | 128/145.8 |
| 3,817,246 | 6/1974 | Weigl | 128/145.8 |
| 3,840,006 | 10/1974 | Buck et al | 128/145.8 |
| 3,861,385 | 1/1975 | Carden | 128/145.8 |

Primary Examiner—Robert W. Michell
Assistant Examiner—Henry J. Recla
Attorney, Agent, or Firm—Lothrop & West

[57] ABSTRACT

A volume ventilator effective to give a patient successive inhalations and exhalations at timed intervals is responsive to the patient's effort to inhale and at selected times gives the patient a deep breath synchronized with the patient's effort to inhale.

8 Claims, 4 Drawing Figures

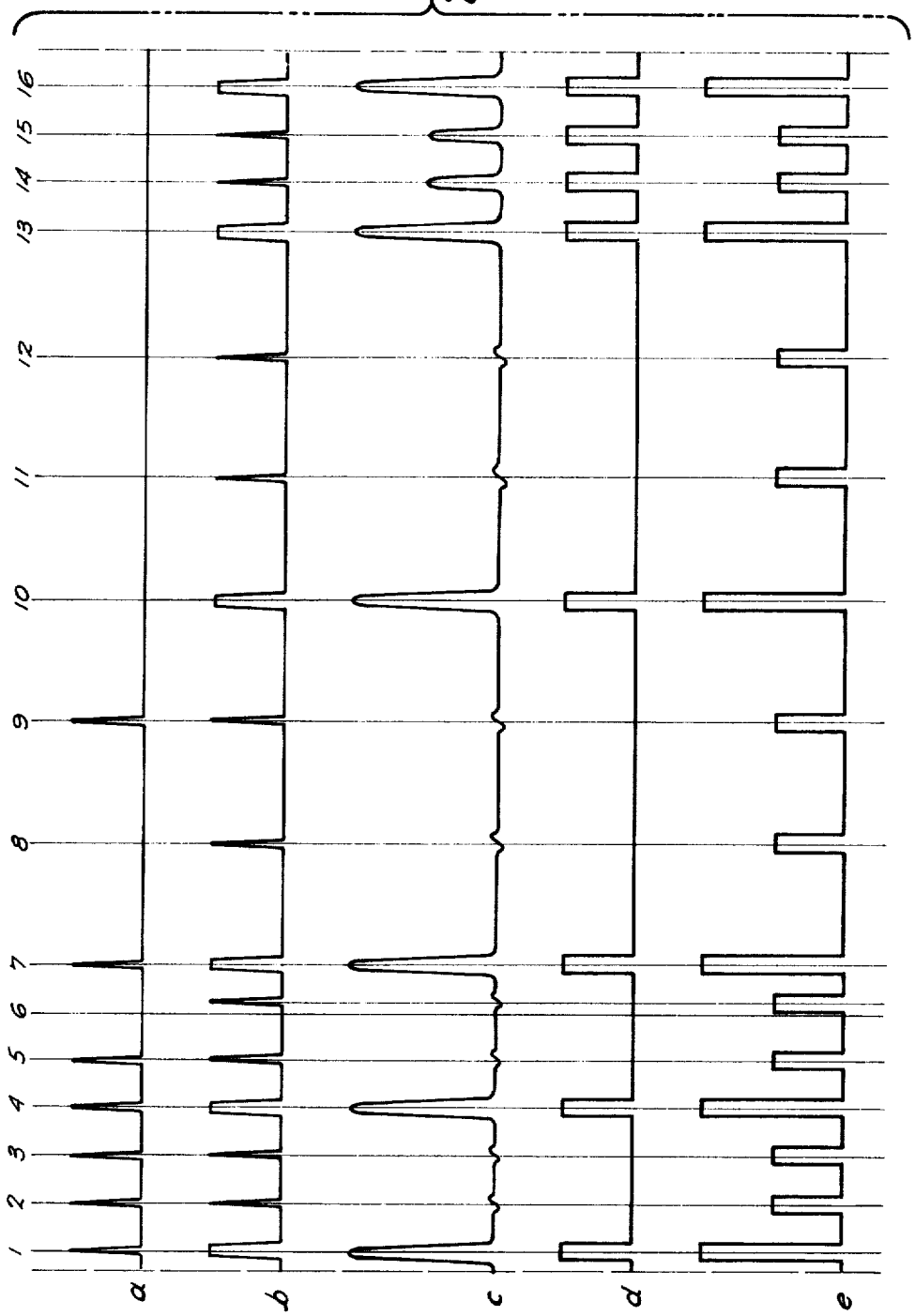

INTERMITTENT DEMAND VENTILATOR

Particularly for patients who have been mechanically ventilated but who are again able to breathe on their own, at least for some time, and particularly to care for such patients while they are becoming accustomed to getting along without mechanical assistance, there is a need for furnishing a deep breath from time to time, preferably as initiated by the patient and in synchronism with his own breathing. It is preferred to give him a proper mixture of air and oxygen (humidified) to breathe with or without assistance and for the desired deep breaths.

As shown in U.S. Pat. No. 3,840,006, issued Oct. 8, 1974, there is a respirator or a volume ventilator for adults, referred to as a "VVA", having the capability of ventilating a patient and also effective, when a button is manually pushed, to give the patient a deep breath. In view of the desire to afford deep breaths at generally regular, chosen intervals and not only to patients who are mandatorily being ventilated but also to those who are merely being assisted in breathing, there is need for a mechanism that will achieve this result, preferably in consonance with the patient's own efforts.

It is therefore an object of the invention to provide a device to afford a patient a mandatory deep breath at chosen intervals and to initiate the deep breath cycle coincidentally with the initiation of inhalation by the patient.

Another object of the invention is to provide a device in the form of an adjunct or addition to a device as disclosed in the above-identified patent to afford additional capability to the device of the patent.

A further object of the invention is to provide a device that is especially useful with patients not normally needing assistance in their own breathing and capable of initiating inspiration on their own, to impress a deep breath cycle at selected intervals but in time with the patient's own breathing.

An additional object of the invention is to provide a device that can readily be applied to an existing device, as shown in the above-mentioned patent, to afford timed and synchronized deep breath cycles.

A further object of the invention is in general to provide an improved and more versatile ventilator.

Other objects, together with the foregoing, are attained in the embodiment of the invention, described in the following description and illustrated in the accompanying drawings, in which:

FIG. 4 is a diagram on a time basis illustrating the relationship of various events in the operation of the intermittent demand ventilator.

Figure 1:
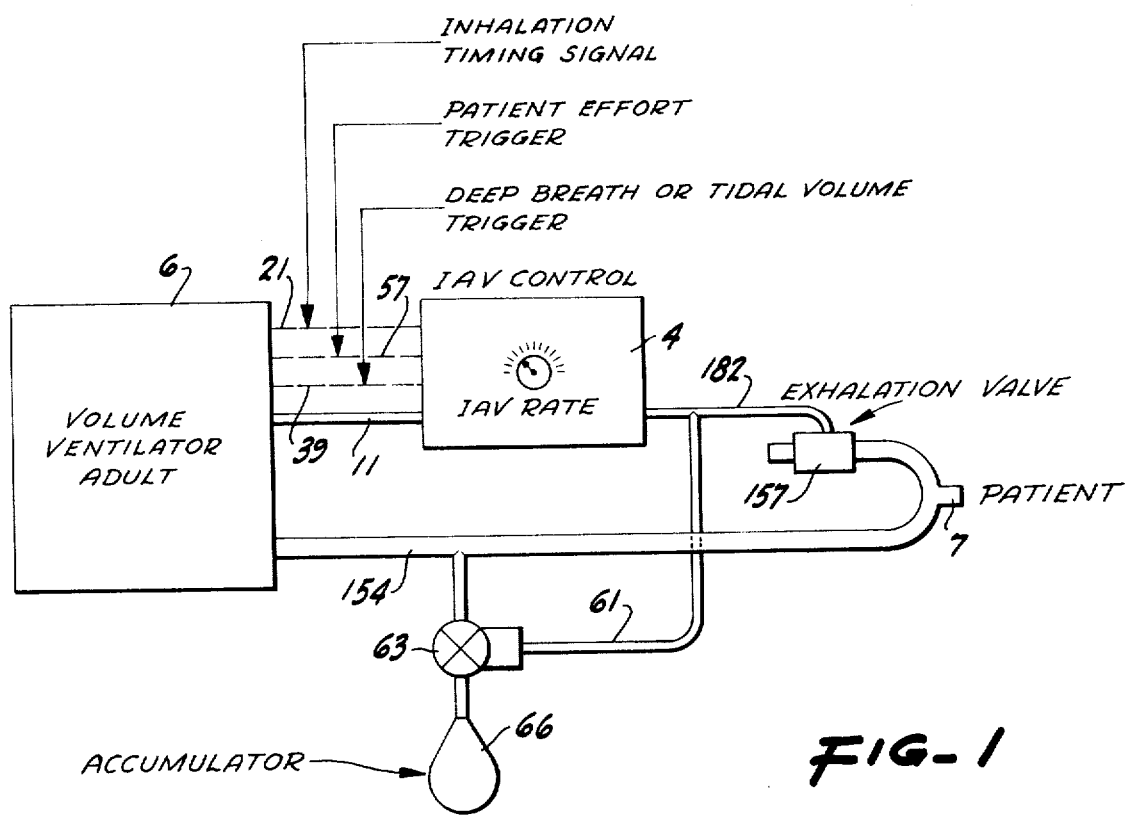
FIG. 1 is a diagram of a device in accordance with this arrangement, particularly one in which the device is in the form of an attachment or addition to an existing ventilator.
Figure 2:
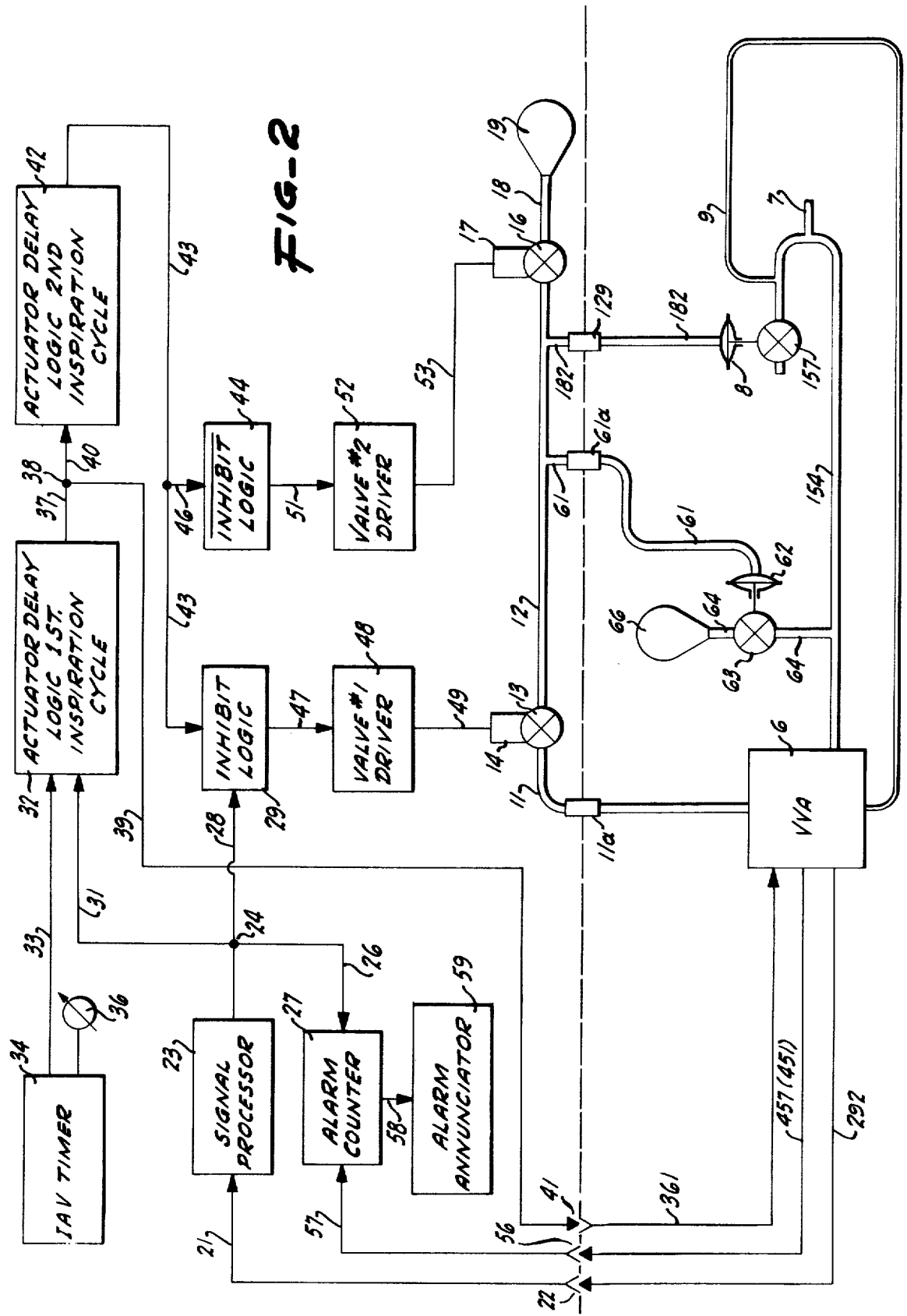
FIG. 2 is a diagrammatic showing of pneumatic and functional paths involved in the present intermittent demand ventilator.

The mechanism for use with the indicated VVA can be considered so far as it is necessary herein with some of the same reference numbers utilized in the patent, to which reference is made for mechanism not repeated herein. The VVA itself is designated generally by a block 6 from which extends an airway 154 having a fitting 7 which is made available immediately to the patient and having an exhalation valve 157 which can be opened and closed to afford communication with the atmosphere under control of a valve actuator 8 (FIG. 2). Pressure within the airway 154 is transmitted by a tube 9 which extends between the airway near the fitting 7 to the enclosure 6 for the VVA. Such pressure is utilized within the mechanism 6 for actuating various controls. While there is normally and in the VVA of the patent a direct connection from the machine 6 to the valve actuator 8, in the present instance the connection is somewhat circuitous. That is because there is supplied an additional unit 4 (FIG. 1) preferably mounted on and having connections to the circuitry of the VVA 6. For example, from the machine 6 there extends a conduit 11 open to the airway 154 and having a connector 11a joined to an intermediate pipe 12 in turn having a connection 129 in a joined tube 182 supplying pressure fluctuations to the diaphragm of the actuator 8 for controlling the valve 157.

According to the invention there is specially interposed in the pipe 12 a normally open valve 13 having an electric closing actuator 14 incorporated therewith. A normally closed valve 16 having an electric opening actuator 17 is also interposed in the line 12 and joins a line 18 open to a positive end expiration pressure reservoir 19, balloon or accumulator, as shown in the patent.

A conductor 21 provided with a detachable fitting 22 joins to a conductor 292 within the VVA 6 and is effective to carry a signal from the VVA 6, referred to as an inspiration signal. The conductor 21 goes into a signal processor 23. If the incoming signal is ragged or of irregular shape the processor provides a corresponding output signal but of regular and well-recognized shape. A good inspiration signal is thus conveyed to a junction 24.

From the junction 24 the inspiration signal can proceed in three paths. One of the paths from the junction 24 is through a conductor 26 into an alarm counter 27. This receives individual signals and accumulates them and can be reset to cancel such signals. Another path for signals from the junction 24 is through a conductor 28 into an inhibit logic board 29. The third path for signals from the junction 24 is through a conductor 31 into an actuator delay logic circuitry 32.

The electronic circuitry 32 not only receives and holds a signal entering through the conductor 31 but likewise receives a signal from time to time through a parallel conductor 33 emanating from a timer 34. This is an intermittent assisted ventilation timer or IAV timer and is provided with a manually adjustable regulator 36. The timer 34 can be set to be sensitive to time intervals over a selected range; for example, 3 seconds to 300 seconds.

From the actuator delay logic mechanism 32 a conductor 37 goes to a junction 38. The signal at the junction is divided into two portions. One portion travels through a conductor 39 and through a connector 41 to a conductor 361 in and forming a usual part of the VVA 6. In the VVA, a manual push button, when depressed, sends a signal through the conductor 361 to provide the patient mandatorily with one, complete, deep breath cycle. The conductor 39 when energized can supply a comparable signal to the conductor 361 with the same result, and this can alternatively be done with the VVA Tidal Volume control.

The other portion of the signal at the junction 38 is carried forward through a conductor 40 to a second, actuator delay logic mechanism 42 able to hold a signal for a time. The output signal from the board 42 is carried through a conductor 43 extending to the inhibit logic board 29 and is also carried through a branch 46 extending to a negative inhibit logic board 44.

From the first inhibit logic board 29, a conductor 47 carries the signal to a driver 48 connected through a conductor 49 to the solenoid actuator 14 of the first valve 13. Similarly, from the second, negative inhibit logic board 44 a conductor 51 extends to a driver 52 joined through a conductor 53 to the solenoid 17 actuating the valve 16.

The remaining electrical connection between the VVA 6 and the present attachment 4 is a patient effort conductor 457 (or 451) which goes through a connector 56 to a conductor 57 carrying a signal to the alarm counter 27. If desired, the counter 27 may be provided with an output conductor 58 joined to an alarm annunciator 59.

The pneumatic structure is augmented by a tube 61 joined to the pipe 12 through a connector 61a and extending from an operator 62. This is for a valve 63 interposed in a line 64 at one end connected to the airway 154 and at the other end connected to an expansible chamber 66, balloon or accumulator, having a compliance comparable to that of the normal lung compliance of a patient.

In the usual operation of this structure with a patient able to breathe or at least initiate breathing by himself and at a reasonable rate, the VVA 6 is first set to provide mechanically initiated and assisted breathing at a somewhat lower rate. This is a sort of stand-by, for if the patient slows down and falters in his breathing, the machine continues for him albeit at the set, slower rate. During his unassisted breaths the machine still provides him with an oxygen-air breathing mixture available to him at about the ambient pressure or, if the operator so sets the controls, at a chosen positive end expiration pressure.

The breathing and time relationships are diagrammatically represented in FIG. 4 in which separate graphs a, b, c, d and e are shown all on the same time base and with the ordinate dimension roughly approximating certain breathing events. For example, as shown in graph a, the patient by starting his own inhalation has triggered at regular intervals breaths one to five. Graph b indicates the corresponding machine response which has given the patient large or deep breaths for breaths 1 and 4. The patient's triggering effort is shown in graph c by a slight dip or pressure drop in the airway 154 followed by a substantial increase and then decrease in airway pressure for each deep breath, such as 1 and 4, and with only minor pressure fluctuations for normal, unassisted breaths, such as 2 and 3. The timing of closure of the exhalation valve 157 is indicated in graph d showing such valve to be closed for the deep breaths 1 and 4. The increased tidal volume for the deep breaths, such as 1 and 4, is shown by the high blocks in graph e which also illustrates the normal tidal volume for normal breaths, such as 2 and 3.

Should the patient falter and not start to inhale at his usual interval for breath 6 this is detected after a short time by the machine, according to graph b which then gives him a machine-assisted breath 7, a deep breath. If he fails again at breath 8, the ventilator gives him a normal breath and if he initiates breath 9, he takes a normal volume unassisted. Should he stop his own inhalation, as in breaths 10 to 16, he still gets an assisted large inhalation for breath 10 and two assisted regular inhalations for breaths 11 and 12, as before. Breath 13, however, follows three patient untriggered inhalations and so is not only an assisted or mandatory deep breath but also increases the tidal volume and sounds an alarm. Following this, for breaths 14 and 15, still not triggered by the patient, the exhalation valve is closed and the normal tidal volume is furnished mandatorily. The same is true of breath 16 except the volume is large for a deep breath. In sum, breaths 1, 4, 7, 10, 13 and 16 are mandatory deep breaths; breaths 2, 3, 5 and 9 are patient triggered, non-assisted breaths while breaths 6, 8, 11, 12, 13, 14, 15 and 16 are machine initiated.

The timer 34 is set at a value selected by the physician for timing the intervals between the required or imposed deep breaths but only approximately arranges the time of their initiation. For example, the timer 34 may be set to 60 seconds. That is, the interval between successive, mandatory deep breaths is approximately 60 seconds.

When the device is in starting conditions, the valve 13 is normally open, whereas the valve 16 is normally closed. When the patient is connected to the fitting 7 and starts voluntarily to inhale, the cycle is started by a resulting drop in pressure in the airway 154. The lowered pressure in the airway 154 is conducted through the tube 9 to the respirator 6 and triggers the respirator to send a volume of breathing gas for inspiration through the tube 154 to the patient. At the same time a signal denoting such inspiration travels over the conductor 292 and through the conductor 21 to the signal processor 23 and appears at the junction 24. The signal travels through the conductor 31 to the first actuator delay logic board 32. Assuming the timer 34 has just started and the set, deep breath interval has not yet elapsed, there is as yet no signal present in the conductor 33 so there is no output at this time from the actuator delay logic 32. From the junction 24 the inspiration signal travels to the alarm counter 27 and introduces a single pulse or single count therein.

The same signal from the junction 24 is also conducted through the line 28 and is effective upon the inhibit logic board 29. This sends an impulse through the conductor 47 to the valve driver 48 which is then effective through the conductor 49 and the solenoid actuator 14 to close the valve 13, thus precluding any air flow through the conductor 11 into the pipe 12. This is different from the operation of the VVA 6 alone. Without the present mechanism a similar signal from the VVA 6 is directly effective upon the valve driver 48 to open the valve 13 and pressurize the pipe 12 and tube 182 to close the exhalation valve 157 so the patient is given a forcible inhalation. In this case, the signal to the inhibit logic 29 causes the driver 48 to close the valve 13 and open or keep open the exhalation valve 157.

Figure 3:
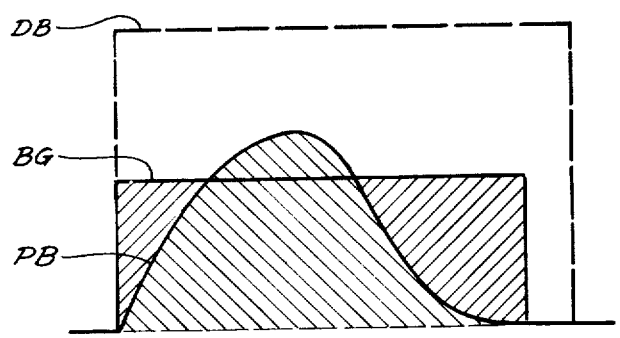
FIG. 3 is a diagram illustrating a single breathing cycle and including a deep breath event.

The pipe 12 is open to the reservoir or accumulator 19 through the normally open valve 16 so at this time there is a relatively low pressure in the pipe 12 and its connections. Thus, there is a corresponding low pressure in the conductor 182 causing the actuator 8 to restrict the exhalation valve 157 accordingly i.e. a small amount. Breathing gas traveling through the tube 154 to the patient's fitting 7 can also escape through whatever small restriction the valve 157 imposes and to the atmosphere. Since some gas escapes the VVA 6 affords an excess breathing gas supply. The patient can inhale as much of it as he likes, at his option, through the airway 154 with any surplus flowing through the partially open exhalation valve 157 to the atmosphere. As shown in FIG. 3, a sample breathing cycle, as controlled by the patient, is represented by a line PB. The excess amount of breathing gas simultaneously supplied, as described, is represented by a line BG. This is less than the peak requirement which is derived from the accumulator 66. Breathing gas is thus mechanically furnished to the patient for him to take in any desired quanity leaving any excess to escape.

When the patient initiates the breathing cycle by inhaling, another signal indicating proper response by him is carried from the VVA 6 and through the conductor 457 (or 451) and the conductor 57 to the alarm counter 27 and cancels the previous input through the conductor 26. However, if the patient does not initiate inhalation for a predetermined number, say three, cycles and so leaves previous impulses from the line 292, 21 and 26 uncanceled and accumulated in the counter, then a signal from the counter 27 goes through the conductor 58 and actuates the alarm annunciator 59 to summon an attendant to inspect and determine the difficulty.

After some cycles of operation, the deep breath set interval expires. A signal is then sent from the timer 34 over the conductor 33 to the board 32 and is delayed or held there and is still present when the next signal from the VVA 6, initiated by the patient, arrives over the conductor 31. The board 32 acts as an "and" gate and with both signals present, or the two precedent conditions satisfied, the delay logic 32 sends a signal over the conductor 37 to the junction 38. That signal travels through the conductor 39 and through the conductor 361 back to the VVA 6. Therein the signal effectively actuates the standard mechanism to afford one deep breath for the patient. Thus, the deep breath is initiated by the patient's inhalation and begins simultaneously with the patient's timing thereof. This is illustrated in FIG. 3 by a line DB indicating that a larger volume of breathing gas is being made available to the patient by the VVA 6 starting with the patient's own effort.

In addition, the patient is made mandatorily to inhale such larger volume. From the junction 38 the signal also travels through the conductor 40 to the second actuator delay logic board 42. This is also a holding or delay device and preferably retains its signal long enough to be triggered by the next signal from the VVA 6 incident upon the patient's starting his next inhalation. Thus, while a first inspiration signal may enter the logic board 32 and may be followed by a signal from the timer 34 and so signal the logic board 42, this may well be after the patient is well along in taking his inspiratory breath. The signal is thus held or delayed in the board 42 until the patient starts his second or next inspiration breath, whereupon the board 42 in response thereto and coincidentally therewith sends out its signal on the conductor 43.

The signal through the conductor 43 goes not only to the inhibit logic board 29 but also to the negative inhibit logic board 44. The signal in the inhibit logic board 29 from the conductor 43 and despite any signal in the board 44 from the conductor 28, is carried to the valve driver 48 which is then effective to cause such driver to de-energize the solenoid 14 and open the previously closed valve 13 so that a control air supply flows from the tube 11 into the pipe 12.

At the same time the same signal in the negative inhibit logic board 44 actuates the valve driver 52 to send a signal through the line 53 to deenergize the solenoid 17 so that the previously open valve 16 is closed to preclude communication with the accumulator 19. Pressure within the pipe 12 then builds up. Such pressure is transferred through the tube 182 to actuate the actuator 8 closing the exhalation valve 157. The airway 154 is no longer in communication with the atmosphere. The patient is, therefore, made to take the deep breath that he has initiated and has been programmed by the timer 34.

Pressure in the pipe 12 also travels to the tube 61 and causes the actuator 62 to close the valve 63 connecting the balloon 66 to the airway 154. Thus, while the balloon affords extra volume to the airway for peak nonassisted inhalation, it is isolated for mandatory inhalation. The patient is given by machine a predetermined, large supply of breathing gas at a controlled and satisfactory rate and pressure.

At the end of the deep breath cycle the VVA 6 reverts to its normal operation and the electric signals all terminate. The valve 13 again closed and the valve 16 again opens to the accumulator 19. The exhalation valve 157 resumes its variably throttling pressure control function as positioned by the actuator 8 responsive to pressure in the pipe 12 and is again partially open so that the patient is again given at the set PEEP pressure a slight oversupply of breathing gas. He can again inhale from the airway 154 and the accumulator 66 and exhale through the valve 157 at his own will until the timer 34 again sets the mechanism for a mandatory deep breath initiated by the patient's voluntary inhalation.

Should the patient at any time fail to keep his normal inhalation rhythm and falter, his breathing is then controlled by the slower rate, mandatory breathing cycles provided by the initial setting of the machine 6. The device is then time triggered for initiation of inhalation rather than patient triggered, and the deep breath cycle continues at the set intervals and it also is triggered by the ventilator 6 rather than the patient. This slower rate can continue indefinitely or until such time as the patient resumes his own, faster rate inhalation.

What is claimed is:

1. An intermittent demand ventilator comprising a ventilator having a patient airway, an exhalation valve in said patient airway controlling opening of said airway to the atmosphere, an accumulator, a pipe at one end connected to said ventilator to receive air under pressure therefrom and at the other end open to said accumulator, a first valve in said pipe for controlling air flow from said ventilator into said pipe, a second valve in said pipe for controlling air flow between said pipe and said accumulator, means connected to said pipe between said valves for operating said exhalation valve, means responsive to pressure in said airway for providing one of a pair of signals indicative of a sensed lower pressure in said airway due to a patient starting inhalation, a timer means for providing the other of said pair of signals indicative of time intervals between deep breaths delivered to the patient, means responsive to the concurrent existence of said pair of signals for actuating said first valve in an open position and said second valve in a closed position, whereby said exhalation valve is actuated in a closed position and said ventilator delivers a volume of gas equivalent to a deep breath to the patient and responsive to a non-concurrent existence of said pair of signals for actuating said first valve in a closed position and said second valve in an open position whereby said exhalation valve is partially closed by a relatively low pressure in said pipe and accumulator, and means for operating said exhalation valve thereby providing a positive end expiratory pressure in said airway.

2. A device as in claim 1 in which means responsive to pressure in said airway responds to a lowering of pressure therein due to a patient starting inhalation.

3. A device as in claim 1 including means for counting the occurrences of said signal responsive to pressure in said airway, means controlled by said ventilator for zeroing said counting means, and means responsive to a predetermined count in said counting means for actuating an alarm.

4. A device as in claim 1 in which said timer means is settable to a selected time period.

5. A device as in claim 1 wherein said means responsive to the concurrent existence of said signals includes a first delay means for receiving one of said signals from said pressure responsive means and for receiving the other of said signals from said timer means and when both of said signals are present therein for releasing a resulting signal to said valve actuating means.

6. A device as in claim 5 including a second delay means interposed between said first delay mechanism and said valve actuating means.

7. A device as in claim 6 including means interposed between said second delay means and said valve operating means for causing said actuating means to open said first valve and simultaneously close said second valve and vice versa.

8. A device as in claim 1 including a second accumulator, means for connecting said second accumulator to said airway, a third valve in said connecting means, an actuator for said third valve, and means for connecting said third valve actuator to said pipe between said first valve and said second valve.

* * * * *